United States Patent [19]

Daniels

[11] 4,290,432
[45] Sep. 22, 1981

[54] DECOMPRESSION BUBBLE DETECTORS

[75] Inventor: Stephen Daniels, Oxford, England

[73] Assignee: Secretary of State for Defence in Her Britannic Majesty's Government of the United Kingdom of Great Britain and Northern Ireland, London, England

[21] Appl. No.: 83,439

[22] Filed: Oct. 10, 1979

[30] Foreign Application Priority Data

Oct. 11, 1978 [GB] United Kingdom ............... 40103/78

[51] Int. Cl.³ .............................................. A61B 10/00
[52] U.S. Cl. .......................................... 128/660; 73/19
[58] Field of Search ................................ 128/660–663; 73/19, 61 R, 24, 194 A, 432 PS, 596, 609, 642, 861.25

[56] References Cited

U.S. PATENT DOCUMENTS

| | | | |
|---|---|---|---|
| 3,710,615 | 1/1973 | Johnson et al. | 73/61 R |
| 3,921,622 | 11/1975 | Cole | 73/19 |
| 3,974,683 | 8/1976 | Martin | 73/61 R X |
| 3,974,826 | 8/1976 | Eggleton et al. | 128/661 X |
| 4,068,521 | 1/1978 | Cosentino et al. | 128/661 |
| 4,112,775 | 9/1978 | Abts | 73/642 |
| 4,130,010 | 12/1978 | Woun | 73/19 |

OTHER PUBLICATIONS

Furness, A. et al., "Detection of Bubbles in Blood Vessels and Extra-Corporeal Circuits", Med & Biol. Eng & Comput, Jul. 1979, pp. 534–535.

Primary Examiner—Robert W. Michell
Assistant Examiner—Francis J. Jaworski
Attorney, Agent, or Firm—Pollock, Vande Sande and Priddy

[57] ABSTRACT

A decompression bubble detector comprises a pulsed ultra-sound transmitter/receiver which is scanned across a cross-section of tissue and the total number of pulse echoes received in a preselected time interval is recorded. Changes in the total number of pulse echoes recorded in successive time intervals are used to monitor the decompression. A single transducer is scanned by means of a driven eccentric cam and a cam follower. A sin/cos potentiometer generates a signal related to the angular position of the transducer connected to a delay so that pulse counting can be arranged to coincide with the passage of the transducer across the target.

12 Claims, 3 Drawing Figures

DECOMPRESSION BUBBLE DETECTORS

The invention relates to the detection of bubble formation in a diver's tissues during decompression procedures.

The symptoms of decompression sickness have been attributed to both moving and stationary bubbles. A decompression detector should ideally therefore be capable of responding to both types of bubble.

Bubble formation has been studied with ultra-sound which offers a powerful tool for decompression monitoring because of the large attenuation of an ultra-sound beam by a gas bubble. Several ultrasound transmission techniques have been used, however methods based on reflection of ultra-sound have been most widely used since gas bubbles in tissues are highly efficient reflectors. The most extensively used reflection technique has employed Doppler shift measurements to detect moving bubbles. The Doppler systems suffer two major disadvantages in being able to detect only moving and hence intravascular bubbles and being unable to see the formation of bubbles within the cross-section of tissue under observation.

An alternative method is the pulse-echo imaging method which detects both moving and stationary bubbles within a cross-section of tissue. By careful analysis the distribution and movement of any bubbles found can be studied. The analysis of the ultra-sound images has required a considerable time, and this method has not therefore been a suitable direct monitor of decompression procedures.

The object of the invention is to produce a detector which quickly responds to both stationary and moving bubbles in a cross-section of tissue.

The invention consists of an ultrasonic detector for detecting decompression bubbles in human tissue comprising a pulsed ultrasonic transmitter, means to scan the transmitter across an area of tissue, a detector to record echoes reflected from said scanned area of tissue, a counter to count the number of echoes recorded by said detector in a preselected time interval, and a display means whereby the numbers of echoes recorded in successive preselected time intervals can be displayed.

In one advantageous arrangement a single ultrasonic transducer is used for both transmission and detection. Preferably the transducer is circular in cross-section and is provided with a plane-concave lens mounted directly on one face of the transducer whereby the ultrasonic energy is focused on the said area of tissue. Conveniently said transducer is scanned by means of an eccentric cam and follower drive system. Advantageously the transducer is held in a fixed position relative to a target and is acoustically coupled thereto by water or an isoosmotic salt solution. In an alternative arrangement a transducer array comprising a plurality of transducer elements is used for transmission and detection, scanning being achieved by electrically switching from one of said elements to the next. Preferably the transducer should operate at a frequency between 2.5 and 8 MHz to provide suitable resolution plus penetration. Advantageously the minimum pulse repetition rate used is a minimum consistent with the area being studied.

In a convenient arrangement a trigger pulse initiated by the scanning means starts the counter via a delay unit, the delay being set so that the counting coincides with the passage of the transducer scan across the target. The number of pulse echoes recorded from a typical tissue cross-section in a counting time of 1.5 sec using a pulse repetition frequency of 2 kHz is typically about 10,000. In order that changes in the count can be readily observed this high base-line count is advantageously reduced by subtracting a preselectable number from the count. In a convenient arrangement the numbers of echoes recorded in successive time intervals less said preselected number are displayed by means of a pen recorder.

The invention will now be described by way of example only with reference to the accompanying drawings of which:

Figure 1:
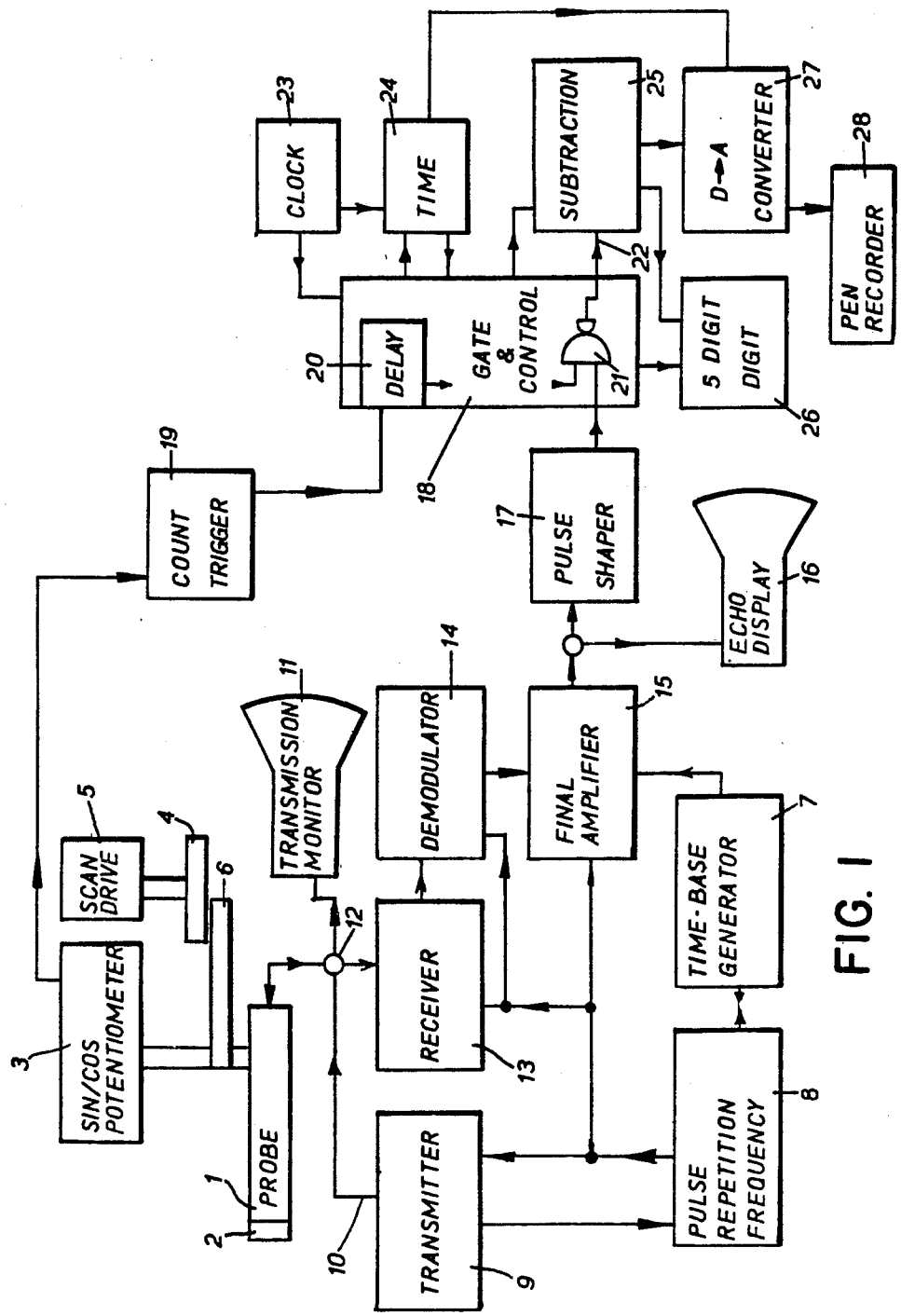
FIG. 1 is a block diagram of the ultra-sound bubble detector.

The decompression bubble detector shown schematically in FIG. 1 uses an integrating pulse-echo technique. A single element circular PZT-5A transducer probe 1 of 5 mm diameter with an operating frequency of 8 MHz is provided with a plano-concave focusing lens 2. The focal length of the lens is 20 mm. The transducer 1 is mechanically linked to a sin/cos potentiometer 3 and a follower drive system. A simple sector scan of about 1 Hz is provided by means of an eccentric cam 4 driven by a motor 5 and a cam follower 6. The sin/cos potentiometer 3 generates a sinusoidal signal related to the angular position of the transducer probe 1 which is used to activate a trigger which initiates pulse counting. The transducer 1 is normally positioned 15 mm behind the target and is acoustically coupled to the target by water or an iso-osmotic salt solution. A time-base generator 7 and a pulse repetition frequency control circuit 8 provide a transmitter trigger which in turn provides a pulse to a transmitter 9 wherein a thyristor discharges preloaded capacitors to the transducer 1 via a HF cable 10. The transducer 1 is chosen to operate at a frequency of 8 MHz so as to provide suitable resolution plus penetration. At 8 MHz, the tissue penetration is about 4 to 5 cm. For scanning across a human thigh a frequency of about 2.5 MHz would be used so as to be able to scan a similar section across the thigh. The pulse repetition frequency of the transmitter 9 is chosen to be 2 kHz. A CRT monitor 11 is provided to monitor the transmitted pulses because any instability which might develop severely affects the reliability of the detector. The CRT monitor 11 is connected to the HF cable 10 between the transmitter 9 and the transducer 1 at a connection 12.

The transducer 1 is also used as the detection element for reflected echo pulses. Echoes are converted by the transducer 1 into electrical signals which are connected to a receiver 13. The receiver 13 includes a 0–80 dB attenuator and an amplifier stage. The receiver output is demodulated by a demodulator 14 and connected to a final amplifier 15. The output from the final amplifier 15 is provided as an input to an echo display CRT 16, and after shaping by a pulse shaper circuit 17 as an input to a gate and control circuit 18 which controls the counting of the echo pulses. The received echo pattern is displayed, firstly to check that the desired penetration is attained and secondly so that the correct level of signal suppression and swept gain compensation is employed. A trigger pulse is generated by a trigger circuit 19 connected to the sin/cos potentiometer 3 so as initiate the echo counting cycle via a delay circuit 20, shown as part of the gate and control circuit 18. The delay of the circuit 20 is set so that the counting coincides with the passage of the scan of the transducer 1 across the target. The control unit 18 has a stored time reference which determines the length of time the gate 21 of the gate and control circuit 18 is open allowing pulses from the pulse shaper 17 to be transmitted to the output 22 of the gate and control circuit 18. On production of a trigger pulse from the trigger circuit 19 the gate 21 is opened and a clock 23 starts to count into a timing circuit 24. When the count in the timing circuit 24 is equal to the stored time reference the control circuit 18 closes the gate 21.

In order that the bubble detector will be sensitive to small increases in the total number of echoes, the echo pulses at the output 22 of the gate and control circuit 18 are connected to a subtraction circuit 25 where a fixed number is subtracted so as to leave a small remainder representing the base-line count. Any increase from the baseline count should then be more clearly observable. The appearance of stationary bubbles will be seen as an increase in the echo count, while bubbles passing through the plane of scan will be seen as an increase in the variability of the count. The number subtracted is determined by inspection of the total number, typically about 10,000 using a pulse repetition frequency of 2 k Hz and a counting time of 1.5 sec. After subtraction the remaining pulses are fed to a digital count display unit 26 and are also passed through a divide-by-ten circuit (not shown) to a Digital-to-Analogue (D/A) converter 27. The D/A converter 27 is such as to accept 256 digital levels and the divide-by-ten circuit is used so that the echo remainder can be set at approximately 250 (typically 1/40 of the total echo count) and a ten-fold increase in the echo remainder can be accommodated. Initially with zero subtraction the digital display 26 registers the total number of echoes. From observation of this number, the number to be subtracted by the subtraction circuit 25 so as to leave a remainder of about 250 is stored in the gate and control circuit 18. From the D/A converter 27 the analogue signal representing 1/10th the echo remainder is fed to a pen recorder 28.

In an experimental arrangement to test the decompression bubble detector a male guinea pig was anaesthetised. The hind limbs were shaved and all remaining hair removed with a depilatory cream. Electrocardiogram (ECG) electrodes were attached, one at the back of the neck and one positioned directly over the heart. The guinea pig was then placed inside a perspex holder designed so that the hind limbs were readily accessible to the ultra-sound transducer. The holder was then fixed into a perspex scanning tank and a brass framework carrying the transducer, the sin/cos potentiometer and the drive system was positioned behind the guinea pig. The position of the transducer was adjusted so as to be 15 mm behind the left hind limb, approximately midway between the knee and ankle and with the leg central with respect to the axis of the transducer. The entire scanning assembly was placed inside a 36 liter decompression chamber. The scanning tank was filled with the iso-osmotic solution comprising 0.7% NaCl, 0.035% KCl and 0.03% $MgSOk_4.7H_2O$ w/v in water so that the test limb and transducer were completely covered. The salt solution had been preheated to 37° C. and was maintained at 37° C. throughout the experiment by a thermostatically controlled heating element located in the bottom of the scanning tank. Soda lime scrubbers were placed inside the chamber and the chamber sealed. An internal fan was provided to ensure adequate mixing and scrubbing of the chamber gases. The pressure was then increased using medical grade compressed air to a pressure of 8.3 bar (120 p sig) over 1 min. This pressure was maintained for 90 mins, a period sufficient for saturation to be reached. The ambient chamber temperature throughout the experiment was 30±1° C.

The ultra-sound system was switched on 5 min before decompression and adjusted to a gain of 75 dB and a pulse repetition rate of 2 kHz. Swept gain was set to compensate for the attenuation of echoes from deep structures due to absorption. The signal supression was set to eliminate small amplitude, unwanted echo signals. With these settings the total echo count, with a counting interval of 1 sec, was approximately 4,900. Accordingly the subtraction level was set at 4400 to give a zero base-line corresponding to a count of 500 with a full scale deflection corresponding to a count of 2560. When the ultra-sound system was set the guinea pig was decompressed to 0 bar (surface) in 70 sec.

Figure 2:
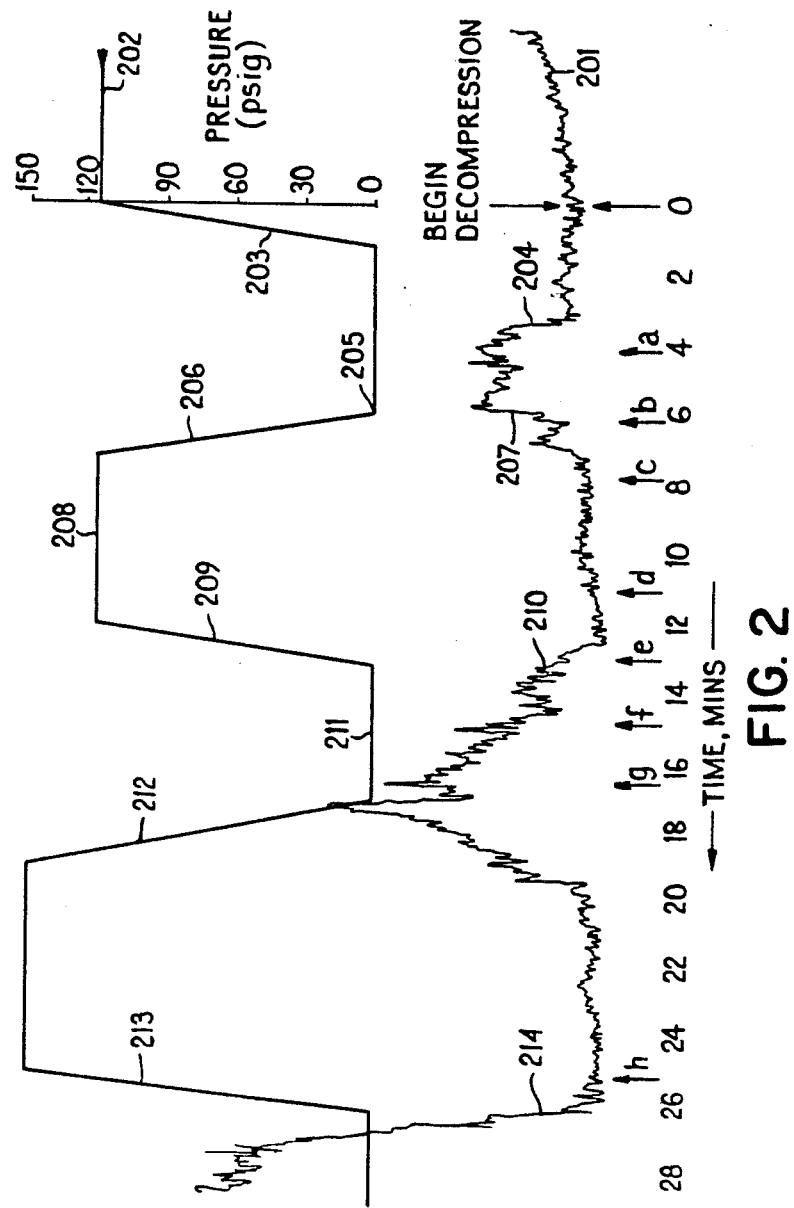
FIG. 2 shows the output recorded by the detector scanning a guinea pig hind leg after a saturation dive to 8.3 bar (120 psig) air.

FIG. 2 shows the echo count 201 as a function of time (increasing to the left) as a result of applying the presure cycle 202 to the guinea pig. The Figure also shows the times of ECG changes indicated by a-g. The count level did not show any change until 3 min 10 sec after the first decompression 203. A rapid increase 204 of about 100% occurred. No change was observed in the ecg until 4 min 10 sec post decompression (a) when some T wave elevation occured. The guinea pig was held at the surface until 5 min 30 sec post decompression indicated by 205. The ecg demonstrated increasingly severe cardiac arrhythmias over this period and the count level remained elevated with a large variation. At 5 min 30 sec post decompression the guinea pig was recompressed (206) to 8.3 bar in 85 sec. The count level fell rapidly (207) in response to the increase in pressure and the ecg returned to a normal form (b). During the period at pressure (208) some periods of T wave elevation (c) were observed and the count level showed bursts of variability outside the normal. At the time d the ecg reverted to normal. After about 5 mins at 8.3 bar (208) the guinea pig was again decompressed (209) to the surface in 70 secs. This time the count level began to rise almost immediately (210), although at a slightly slower rate than previously. Again coupled with this increase in count level there was marked increase in variability. The onset of ecg changes (e) was marked by gross abnormalities. The guinea pig was maintained at the surface (211) for 5 mins during which the heart beat at half the normal frequency (f) and then there developed a low frequency ventricular rhythm with no detectable atrial beat (g). The guinea pig was then recompressed (212) to 8.9 bar in 100 secs. Again the effect of recompression was to rapidly reduce the count to the base level. However the ecg did not return to normal, even after 6 mins at 8.9 bar, although the count remained constant at the base level. The final decompression (213) produced an immediate sharp rise 214 in the count rate of nearly 500%. Following this, cardiac activity ceased.

The experiment indicates that the bubble detector records increases in bubble count which follow the pressure profile and occur before changes in the ecg. In addition the degree of rise in the count level was directly related to the severity of the decompressions. The form of the output from the detector is particularly easy to interpret, unlike the typical output from a Doppler system.

Figure 3:
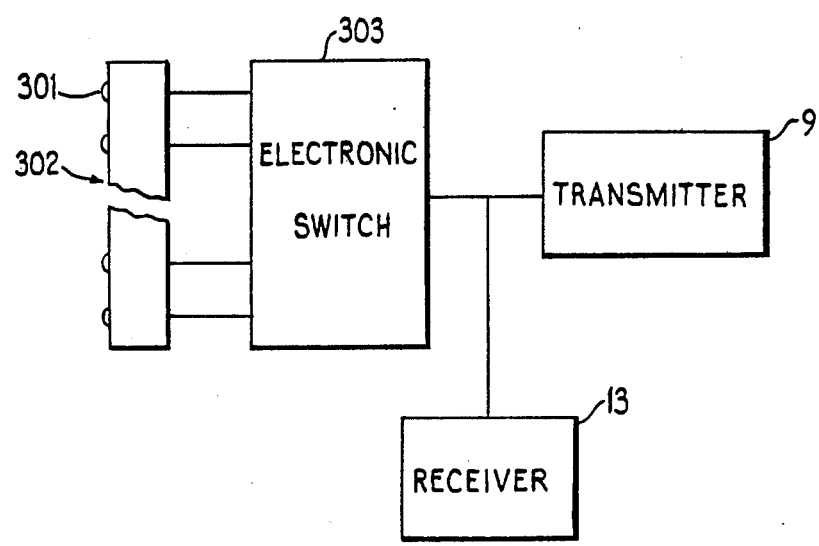
FIG. 3 is a block diagram of a transducer array for use in the ultra-sound bubble detector.

In an alternative arrangement as shown in FIG. 3 the single mechanically scanned transducer is replaced by a plurality of transducer elements 301 forming a transducer array 302, with scanning being achieved by electronically switching from one element to the next by the switch circuit 303. Two possible areas of application for this technique are the detection of vestibular bubble formation and the detection of bubble formation within bone tissue. At present vestibular decompression sickness is the most common manifestation following deep oxy-helium dives. Owing to the efficiency of decomposition therapy bubble formation is thought to be the cause. However such bubble formation has never been observed and indeed with current Doppler techniques could not be seen. The second possibility affords an opportunity of detecting the critical insult to bone tissue and thus, in principle, a means of preventing dysbaric osteonecrosis. Currently this condition can only be diagnosed by radio-graphical methods after deposition of calcium has occurred.

Other methods of processing the ultrasonic pulse echoes within the scope of the invention will be apparent to those skilled in the art.

What is claimed is:

1. A decompression bubble detector for detecting decompression bubbles in human tissue comprising a pulsed ultrasonic transmitter, means to scan the transmitter across an area of tissue, a detector to record echoes reflected from said scanned area of tissue, a counter to count the number of echoes recorded by said detector in consecutive preselected time intervals, means for subtracting from said recorded number of echoes a number substantially equal to the average number of echoes recorded at normal atmospheric pressure, and a display means for displaying the resultant difference numbers of echoes recorded in successive preselected time intervals.

2. A decompression bubble detector according to claim 1 wherein a single ultrasonic transducer is used for both transmission and detection.

3. A decompression bubble detector according to claim 2 wherein the transducer is circular in cross-section and is provided with a plano-concave lens mounted directly on one face thereof whereby the ultrasonic energy is focused on the said area of tissue.

4. A decompression bubble detector according to claim 3 wherein the transducer is held in a fixed position relative to a target and is acoustically coupled thereto by an iso-osmotic salt solution, and said transducer is scanned by means of an eccentric cam and follower drive system.

5. A decompression bubble detector according to claim 4 wherein the transmitter operates at a frequency between 2.5 and 8 MHz to provide suitable resolution plus penetration.

6. A decompression bubble detector according to claim 5 wherein a trigger pulse initiated by the scanning means starts a counter via a delay unit, the delay being set so that the counting coincides with the passage of the transducer scan across the target.

7. A decompression bubble detector according to claim 1 wherein there is provided a transducer array comprising a plurality of transducer elements for transmission and detection, scanning being achieved by electronically switching from one of said elements to the next.

8. A decompression bubble detector according to claim 7 wherein the transducer is circular in cross-section and is provided with a plano-concave lens mounted directly on one face thereof whereby the ultrasonic energy is focused on the said area of tissue.

9. A decompression bubble detector according to claim 8 wherein the transmitter operates at a frequency between 2.5 and 8 MHz to provide suitable resolution plus penetration.

10. A decompression bubble detector according to claim 9 wherein a trigger pulse initiated by the scanning means starts a counter via a delay unit, the delay being set so that the counting coincides with the passage of the transducer scan across the target.

11. A decompression bubble detector according to claim 7 wherein the transmitter operates at a frequency between 2.5 and 8 MHz to provide suitable resolution plus penetration.

12. A decompression bubble detector according to claim 11 wherein the transducer is circular in cross-section and is provided with a plano-concave lens mounted directly on one face thereof whereby the ultrasonic energy is focused on the said area of tissue.

* * * * *